United States Patent
Wehrmeyer et al.

(10) Patent No.: US 6,308,564 B1
(45) Date of Patent: Oct. 30, 2001

(54) METHOD AND APPARATUS FOR DETERMINING THE QUANTITY AND QUALITY OF A FLUID

(75) Inventors: Volker Wehrmeyer, Königstein; Wolfgang Porth, Frankfurt; Werner Wallrafen, Hofheim/Ts.; Joachim Acht, Frankfurt, all of (DE)

(73) Assignee: Mannesmann VDO AG, Frankfurt (DE)

( * ) Notice: Subject to any disclaimer, the term of this patent is extended or adjusted under 35 U.S.C. 154(b) by 0 days.

(21) Appl. No.: 09/154,561

(22) Filed: Sep. 16, 1998

(30) Foreign Application Priority Data

Sep. 23, 1997 (DE) .............................. 197 41 892

(51) Int. Cl.[7] .......................... G01F 23/00; G01N 25/02
(52) U.S. Cl. .............................. 73/304 R; 73/149; 73/75; 73/335.05; 73/25.05; 73/295; 338/38; 374/21; 374/27
(58) Field of Search .................. 73/304 R, 113, 73/335.05, 25.05, 75, 753, 53.01, 295, 149; 338/38, 27; 374/16, 20, 141, 156, 27, 21; 340/449, 450.1, 622; 188/1.11 E, 1.11 R

(56) References Cited

U.S. PATENT DOCUMENTS

| | | | |
|---|---|---|---|
| 2,295,570 | * | 9/1942 | Dunmore ............................ 73/335.05 |
| 2,737,810 | * | 3/1956 | Witte ....................................... 73/362 |
| 3,252,322 | * | 5/1966 | Pring ........................................ 73/113 |
| 3,760,352 | * | 9/1973 | Marcoux .................................. 73/295 |
| 4,059,006 | * | 11/1977 | Mizutani et al. ..................... 340/236 |
| 4,619,140 | * | 10/1986 | Kuhnel ................................ 73/304 R |
| 4,625,284 | * | 11/1986 | Suzuki .................................... 73/313 |
| 4,869,596 | * | 9/1989 | Klein et al. ............................ 374/27 |
| 5,660,052 | * | 8/1997 | Kenyon et al. ......................... 73/753 |

FOREIGN PATENT DOCUMENTS

| | | |
|---|---|---|
| 3148383 | 6/1983 | (DE) . |
| 3515767 | 11/1986 | (DE) . |
| 3603539 | 8/1987 | (DE) . |
| 3639664 | 6/1988 | (DE) . |
| 4002792 | 8/1991 | (DE) . |
| 4113443 | 10/1992 | (DE) . |
| 0510663 A1 | * 4/1992 | (EP) . |

* cited by examiner

Primary Examiner—Hezron Williams
Assistant Examiner—Michael Cygan
(74) Attorney, Agent, or Firm—Martin A. Farber

(57) ABSTRACT

A method and an apparatus are proposed for determining and/or monitoring the quantity and quality of a fluid in which a lowering of the boiling temperature is symptomatic of a deterioration in quality. For this, the filling level and the condition of the fluid—in particular a hygroscopic fluid—are determined successively one after the other by a single sensor of a measuring instrument.

5 Claims, 3 Drawing Sheets

METHOD AND APPARATUS FOR DETERMINING THE QUANTITY AND QUALITY OF A FLUID

FIELD AND BACKGROUND OF THE INVENTION

The invention relates to a method and an apparatus for determining and/or monitoring the quantity and quality of a fluid in which a lowering of the boiling temperature is symptomatic of a deterioration in quality. This is the case in particular with hygroscopic fluids, for example with glycol-based brake fluids or with engine oil.

Since the boiling point of brake fluid is known to be lowered by absorption of water, with the result that the serviceability of the brake is reduced if the brake fluid is strongly heated, monitoring the state of the brake fluid is particularly important. Furthermore, it is also expedient in this connection to establish the filling level of the brake fluid in the hydraulic system.

DE 36 39 664 C2 already discloses a method and an apparatus for monitoring the state or the condition of a hydraulic fluid, the boiling point being determined with the aid of sensor elements. Apart from the boiling point, the momentary temperature of the fluid is measured. As a measure of the temperature difference between the boiling point and the momentary temperature, a so-called "thermal reserve" is formed and displayed.

DE 41 13 443 C2 discloses an apparatus for detecting a liquid or gaseous medium, in particular a fluid filled to a certain level in a vessel, having at least one sensor unit which can be brought into contact with the medium. For this purpose, a heating element and a temperature sensor are used, the influencing of the temperature sensor by the heating element taking place in a way dependent on the presence or absence of fluid of the medium to be tested.

SUMMARY OF THE INVENTION

Against this background, the invention is based on the object of specifying a method and apparatus with which both the filling level or the quantity and the condition or quality of a fluid are automatically determined in a simple but reliable way.

This object is achieved according to the invention by both the filling level and the condition of the fluid—in particular a hygroscopic fluid—being determined successively one after the other by a single sensor of a measuring instrument.

The method according to the invention has the advantage that the determination or measurement of the quantity and quality of the brake fluids in the system can be carried out at any time and by personnel who are not specially trained, without taking an inordinate amount of time. Apart from monitoring brake fluid, the method according to the invention is also suitable for monitoring other fluids, such as engine oil for example.

It has proven to be particularly advantageous for determining the filling level to heat a temperature-dependent resistance element which is located in the system and represents the sensor by applying a current to it and at the same time measuring the voltage across the resistance element, at least two voltage values being used for determining the filling level.

A further advantageous design of the invention comprises determining the condition or quality of the fluid by raising the temperature of the temperature-dependent resistance element by applying to it a current of such an intensity that the boiling temperature of the fluid to be tested is not quite reached if it is of a given quality, by at the same time measuring the voltage across the temperature-dependent resistance element and by comparing this voltage characteristic with the voltage characteristics typical of different qualities.

It is expedient here that the determination of the quality of the fluid takes place only when the entire temperature-dependent resistance element is covered with fluid.

In another embodiment of the invention, it is proposed that, for determining the quality of the fluid, the temperature of a heating. resistance element is increased by applying to it a current of such an intensity that the boiling temperature of the fluid to be tested is not quite reached if it is of a given quality, by at the same time measuring the voltage across the temperature-dependent resistance element when it is supplied with current of low intensity and by comparing this voltage characteristic with the voltage characteristics typical of different qualities.

It has proven to be expedient here for the measured voltage value to be used for calculating the ambient temperature immediately after switching on the current and for the value obtained from this to be stored and taken into consideration when supplying current to the heating resistance element.

It has been found to be an advantageous variant of the invention for the temperature of the fluid to be initially increased by applying current to the sensor containing a temperature-dependent resistance element, by at the same time determining the filling level by measuring the voltage across the temperature-dependent resistance element, by then using this voltage as a criterion for initiating the quality determination or not initiating it if the fluid level is low, by then, if proceeding with the determination of the quality of the fluid, applying to a heating resistance element contained in the sensor a current of such an intensity that the boiling temperature of the fluid to be tested is not quite reached if it is of a given quality, by at the same time measuring the voltage across the temperature-dependent resistance element supplied with current of low intensity and by finally comparing this voltage characteristic with the voltage characteristics typical of different qualities, an automatic signaling of the filling level and quality of the fluid taking place optically and/or acoustically.

In various applications of the method according to the invention, measurements need be performed only at relatively large time intervals, measurements while the motor vehicle is at a standstill being preferable. For this purpose, it is provided in a development of the method according to the invention that the determination of the filling level and/or the determination of the quality of the fluid take(s) place in the time between opening a motor vehicle and starting the engine of the motor vehicle.

An apparatus for carrying out the method according to the invention comprises the sensor arranged in the fluid system being connected to a measuring instrument, which includes on the one hand a current source for supplying current to the sensor and on the other hand a voltmeter for determining the voltage at the sensor, and furthermore comprises the provision of a computer for controlling the measuring sequence and also an optical and/or acoustic display device.

In a development of this apparatus, it is provided that the sensor comprises a temperature-dependent resistance element.

Another development of this apparatus provides that the sensor has in addition to the temperature-dependent resistance element a heating resistance element.

In this case, it is advantageous that the two resistance elements are arranged close to each other. It has proven to be expedient for the heating resistance element to be arranged underneath the temperature-dependent resistance element.

An advantageous application of the apparatus according to the invention is that the hydraulic fluid system is a braking system with a glycol-based brake fluid.

BRIEF DESCRIPTION OF THE DRAWINGS

The invention allows numerous embodiments. Several of these are described below and are diagrammatically represented in the drawing by means of several figures, in which.

DETAILED DESCRIPTION OF THE PREFERRED EMBODIMENTS

Figure 1:
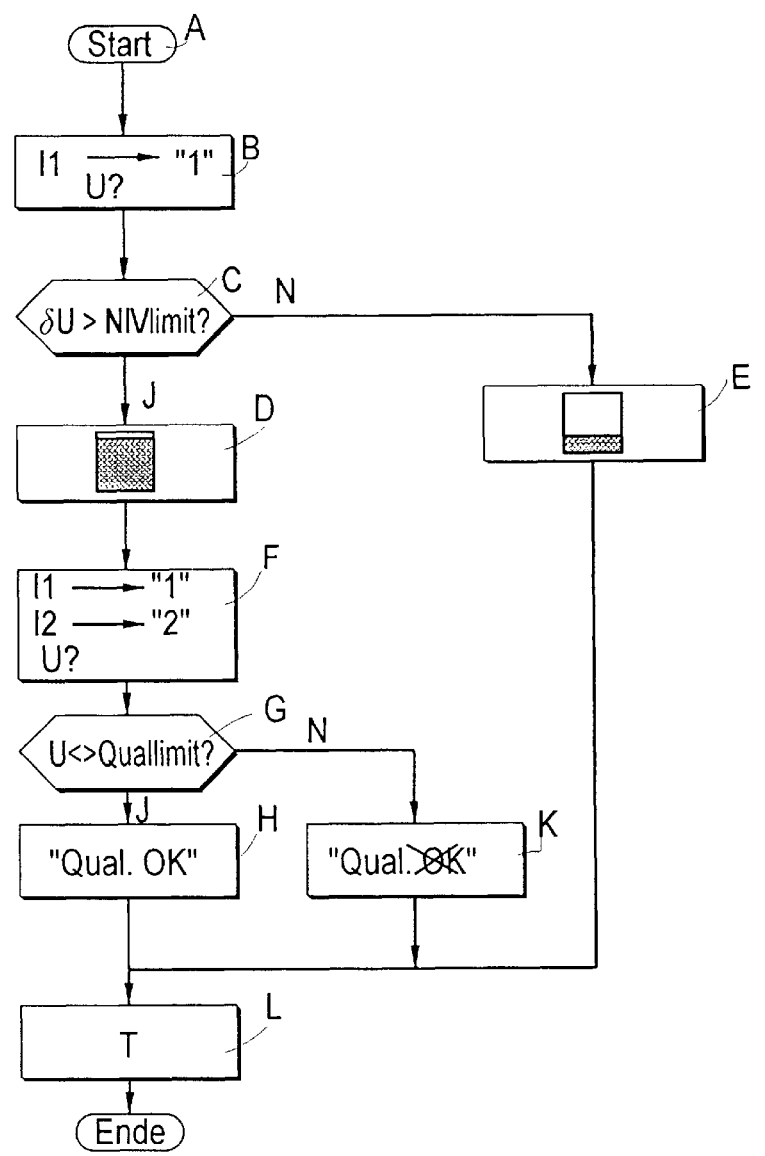
FIG. 1 shows a flow diagram of the method according to the invention for determining the quantity and quality of a hydraulic fluid.

The flow chart represented in FIG. 1 for determining the quantity and quality of a fluid in a hydraulic system may, for example, be stored as a program in a microcomputer. After starting at A, the flow chart proceeds at B for the filling level measurement by applying a current I1 during the time t to the temperature-dependent resistance of the sensor and, at the same time, measuring a voltage U across the temperature-dependent resistance. Then, in the block C, the difference $\delta U = U_1 - U_0$ between the measured voltage values $U_0$ and $U_1$ is compared with the limit value NIVlimit. If the difference $\delta U$, formed from the voltage values $U_0$ and $U_1$, is above the limit value NIVlimit, the message "filling level okay" takes place at the yes output and can be displayed optically and/or acoustically at D. The limit value NIVlimit specified in the block C of the flow diagram is in this case great enough that a quality measurement takes place only if the entire sensor is covered with fluid. If the difference $\delta U$ between the voltage values $U_0$ and $U_1$ is below the limit value NIVlimit, there is emitted at the no output a signal to the effect that a quality measurement is not possible, since the filling level is below a certain level. At E, a corresponding optical and/or acoustic warning message is then emitted.

For measuring the state or quality at F, during the time t on the one hand the temperature-dependent resistance element is supplied with current I1 and, on the other hand, the heating resistance element is supplied with current I2. At the same time the voltage U across the temperature-dependent resistance element 1 is measured.

In the block G, the measured voltage values are then compared with at least one limit value Quallimit, above which a "quality okay" message takes place at the yes output and can be optically and/or acoustically displayed at H. If the voltage characteristic of the measured voltage values lies below one or more limit values Quallimit, there is emitted at the no output of the block G a signal with the effect that an optical and/or acoustic message of the inadequate quality of the fluid is emitted at K. In the case of a brake fluid, the boiling point in the new state is about 200° C., while water absorption may cause the boiling point to drop to 120° C. for example.

The output signals of D or E and K or H are stored. A mandatory waiting time at L prevents the immediate restarting of the sequence at A before the fluid to be investigated has cooled down.

Figure 2:
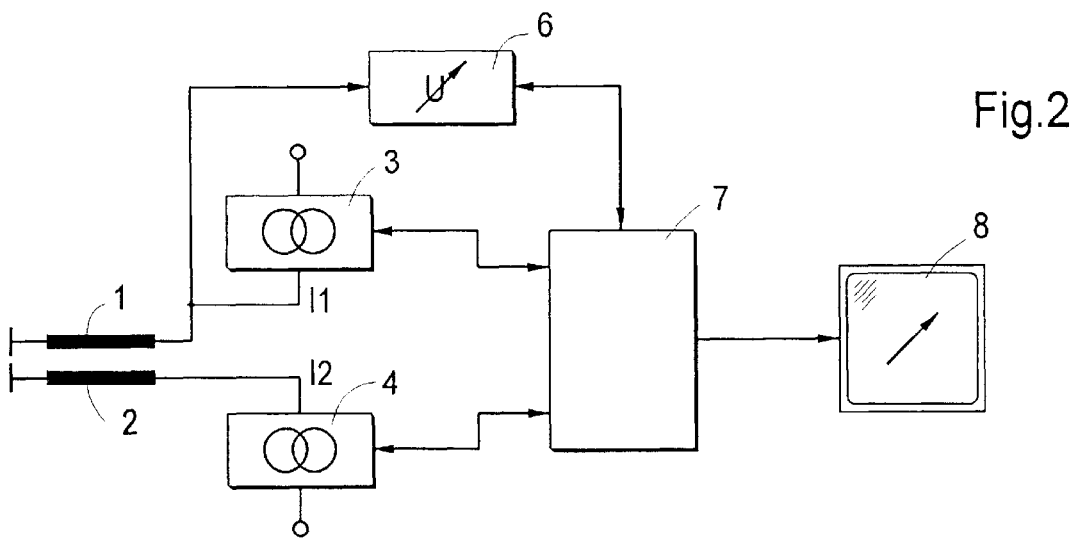
FIG. 2 shows a block diagram of the apparatus for carrying out the method according to the invention.

FIG. 2 shows a block diagram with the temperature-dependent resistance element 1 and the heating resistance element 2, which are connected to current sources 3 and 4 to be provided with current I1 and I2. With the aid of the voltage measuring instrument 6, the voltage U present across the temperature-dependent resistance element 1 is determined at the same time. The sequence of this method is controlled by a microcomputer 7, to the output of which there is also connected an optical-acoustic display device 8.

Figure 3:
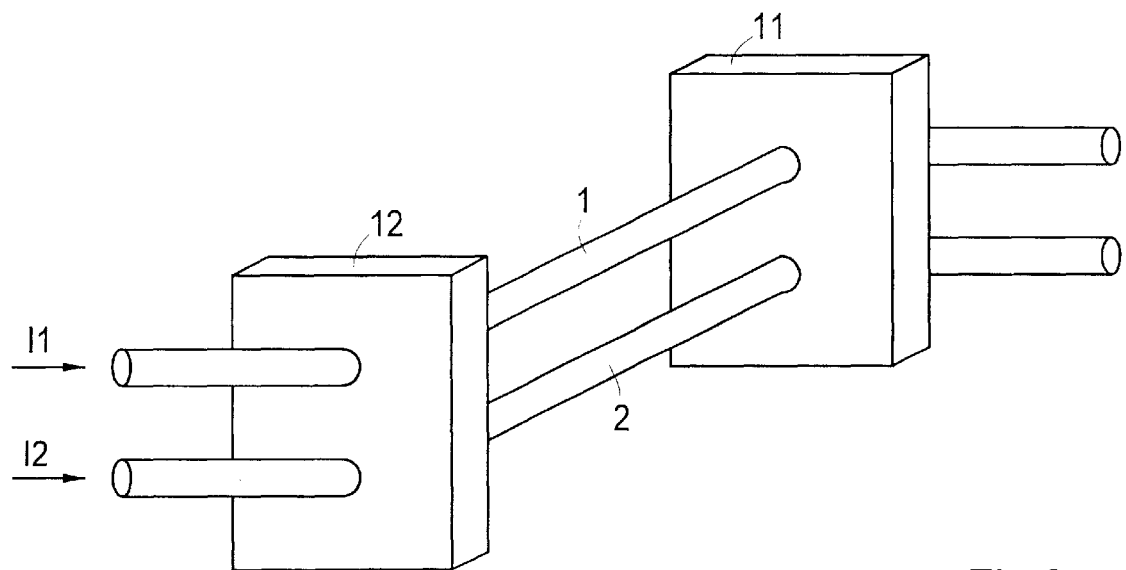
FIG. 3 shows one design of the sensor.

FIG. 3 shows a sensor in a perspective representation. This comprises two resistance elements 1, 2 arranged in the immediate vicinity of each other in holding devices 11, 12, the temperature-dependent resistance element 1 expediently being arranged above the heating resistance element 2.

Figures 4A, 4B, 4C, 4D:
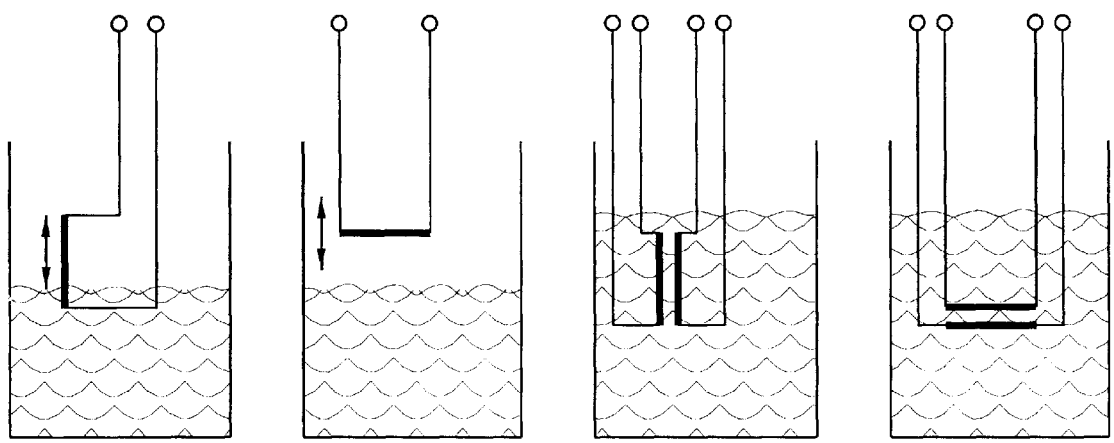
FIG. 4 shows various arrangements of the resistance elements in the fluid.

For filling level or level measurement, only the temperature-dependent resistance element 1 is used; according to FIG. 4a, this resistance element may also be arranged vertically with respect to the fluid level or, according to FIG. 4b, it may be arranged parallel to the fluid level. This resistance element 1 is operated as a heater and resistor simultaneously. Since the dissipation of heat from the resistance element 1 takes place to different degrees inside and outside the fluid, a defined, constant heating current I1 is set in such a way that the different heat dissipation behavior of the resistance element 1 is reflected in a clearly measurable way by a change in its resistance value.

For quality measurement, in addition to the temperature-dependent resistance element 1, the second resistance element 2 is operated as a heating resistance element. The arrangement of the two resistance elements 1, 2 is such that fluid heated or made to boil by the resistance element 2 influences the heat dissipation conditions at the resistance element 1. From at least one voltage U measured across the resistance element 1, a good/bad statement on the quality of the fluid can then be derived by comparison with known voltage values.

The two parallel lying resistance elements 1 and 2 may likewise—as shown in FIGS. 4c and 4d—be arranged perpendicularly, at an angle or parallel to the fluid level, but must always be entirely covered by the fluid for this measurement. To maximize the influence of the heating resistance element 2 on the temperature-dependent resistance element 1, placement of the resistance element 2 underneath the resistance element 1 is advisable.

Figure 8:
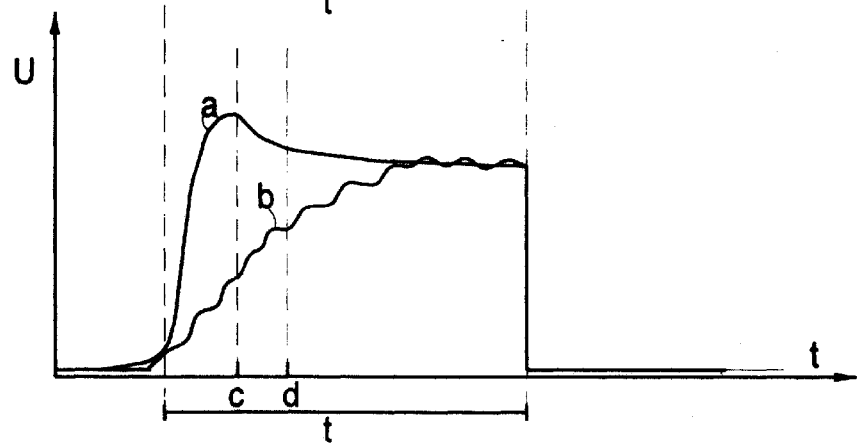

It goes without saying that a measurement of the state is also possible with the resistance element 1 alone, if it is supplied with a current I2 while fully submerged in fluid and the voltage measurement is simultaneously carried out as the time elapses. The evaluation of the voltage characteristic may likewise take place on the basis of characteristic values, as shown in FIG. 8 for example, and leads to a quality statement.

Figure 5:
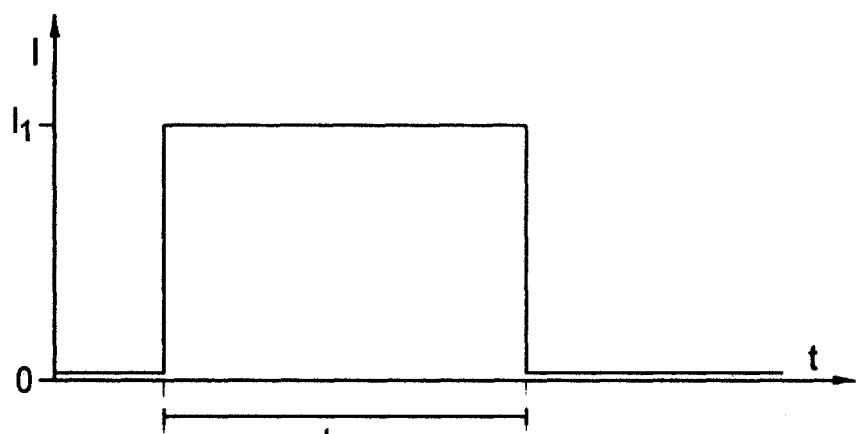
FIG. 5 shows a current/time diagram of the temperature-dependent resistance.
Figure 6:
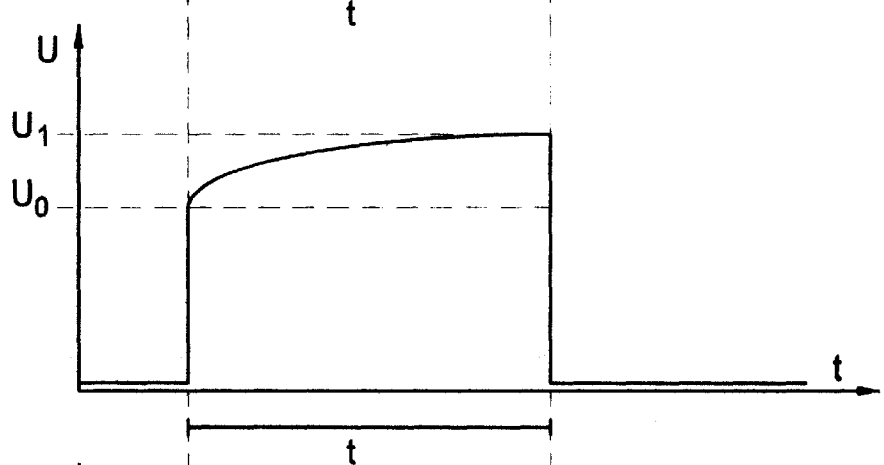
FIG. 6 shows a voltage/time diagram of the temperature-dependent resistance.

According to FIG. 5, the temperature-dependent resistance element 1 dipping obliquely or vertically into the fluid is flowed through by a constant electric heating current $I1$ during a time window t. This causes the element to heat up and, as it does so, to change its electrical resistance. The voltage across the resistance element 1 is measured constantly, or at least at the beginning and end of the current-applying phase according to FIG. 6. The heat of the resistance element 1 is dissipated to a greater degree from its region dipping into the fluid than from its region located above the fluid. Consequently, different fluid levels are reflected by different dissipations of heat and accordingly by a different voltage U across the resistance element 1. The fluid level can consequently be determined from at least two voltages $U_0$ and $U_1$ measured across the resistance element 1.

In the case of the resistance element 1 arranged parallel to the fluid level (according to FIG. 4*b*), the heat dissipation behavior changes abruptly, according to whether the resistance element is within the fluid or outside it. Such an arrangement can establish, for example, the existence of a fluid at a specific filling height.

Figure 7:
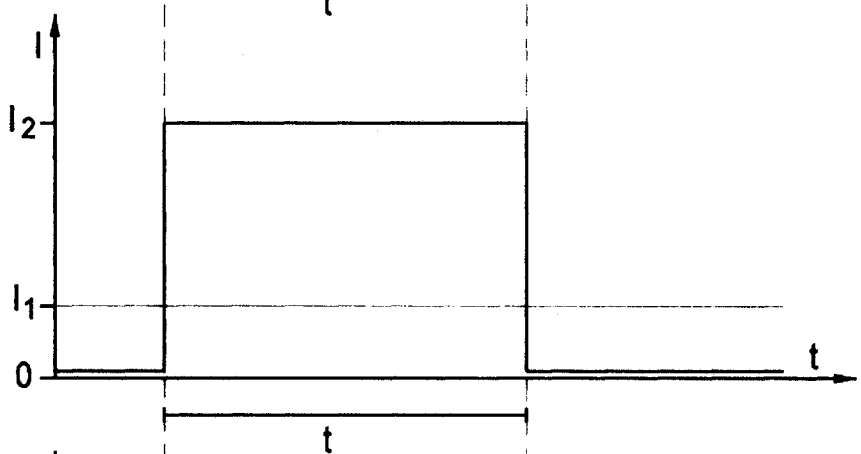
FIG. 7 shows a current/time diagram of the two resistance elements and FIG. 8 shows a voltage/time diagram of the resistance element 1 with the voltage/time characteristic for a fluid of high quality and a fluid of lower quality.

For determining the quality of fluids which decreases with increasing water absorption, which is the case for example with glycol-based brake fluids, the boiling temperature may be used as a measure of quality. The lower the water content of the fluid, the higher its boiling point is known to be, and consequently the higher its quality. To determine this, the further resistance element 2 may then serve as a heating resistance element, which is flowed through by a constant electric current $I2$ during a time window t, according to FIG. 7. The current intensity is in this case chosen such that the boiling temperature of the fluid to be tested is not quite reached at the maximum quality or a given quality. If the quality of the fluid to be checked decreases due to water absorption, the heating resistance element 2 makes the fluid boil. The boiling of the fluid causes the resistance element 1 to then be surrounded by rising bubbles and vapor instead of by fluid. During the measurement, the resistance element 1 is flowed through constantly by a low current $I1$, which serves merely for allowing the voltage across the element 1 to be measured. Accordingly, the current intensity $I1$ during the quality measurement is chosen such that no heating effect emanates from the resistance element 1.

According to FIG. 8, the rise in voltage across the resistance element 1 is more pronounced in a brake fluid of higher quality (curve a) than in a brake fluid of lower quality (curve b). Furthermore, in a brake fluid of lower quality the further progression of the voltage characteristic is less steady and more volatile, since a vaporization takes place when the resistance element 2 is heated up, whereby small bubbles are constantly formed on it and released again. In this case, the coldness produced by the vaporization is to be regarded as temperature-lowering at resistance element 1, accordingly as resistance-influencing. The good/bad evaluation can be realized particularly simply if the voltage level is measured at a number of characteristic points in time (c, d) and is compared with typical voltage values of a good or bad brake fluid.

What is claimed is:

1. A method for determining and/or monitoring the quantity and quality of a fluid in which a lowering of boiling temperature is indicative of a deterioration in quality, wherein both the filling level and the condition of the fluid are determined, the method comprising steps of:

employing a sensor to measure one of said quantity and said quality; and employing said sensor in a successive step of measuring the other of said quantity and quality, said sensor serving as a measurement instrument, said sensor comprising a first resistance element and a second resistance element held in thermal proximity to said first resistance element by a common holder, wherein said first resistance element is a temperature-dependent resistance element and said second resistance element is a heating resistance element, there being a step of immersing both said first and second resistance elements within said fluid;

wherein there is a step of determining the filling level by impressing current to and measuring voltage across the temperature-dependent resistance element, wherein this voltage is then used as a criterion for initiating a quality determination of the fluid if immersion of the resistances is determined, or not initiating the quality determination if the fluid level is low;

wherein a step of determination of the quality of the fluid is accomplished by applying to the heating resistance element a current to heat the fluid to a test temperature less than the boiling temperature of the fluid at the temperature-dependent resistance element if the fluid is of a given quality;

upon attainment of the test temperature in the fluid, supplying current of low intensity to said first resistance element and measuring voltage across said first resistance element, comparing a characteristic of the voltage across the first resistance element with reference voltage characteristics typical of different qualities of the fluid to determine fluid quality, and signaling the filing level and quality of the fluid optically and/or acoustically.

2. The method as claimed in claim 1, wherein, in said step of measuring quantity, the quantity is a filling level, said quantity measuring step including steps of:

employing said first temperature-dependent resistance element which is to be located in the fluid;

heating the first resistance element by applying a current to it, and concurrently measuring the voltage across the first resistance element; and utilizing at least two voltage values for determining the filling level.

3. The method as claimed in claim 2, wherein the determination of the quality of the fluid takes place only when the entire temperature-dependent resistance element is covered with fluid.

4. The method as claimed in claim 2, further comprising a step of employing a measured voltage value for calculating ambient temperature immediately after switching on the current to the heating resistance element, and wherein the value obtained from the calculating step is stored and taken into consideration when supplying current to the heating resistance element.

5. The method as claimed in claim 1, wherein the determination of the filling level and/or the determination of the quality of the fluid take(s) place in an interval of time between opening a motor vehicle and starting the engine of the motor vehicle.

* * * * *